United States Patent [19]

Gregory

[11] Patent Number: 4,808,282

[45] Date of Patent: Feb. 28, 1989

[54] ALKALINE EARTH METAL COMPOUNDS AND ALKALI METAL SUBSTANCES VIA ELECTROCHEMICAL PROCESS

[75] Inventor: Thomas D. Gregory, Midland, Mich.

[73] Assignee: The Dow Chemical Company, Midland, Mich.

[21] Appl. No.: 482

[22] Filed: Jan. 5, 1987

[51] Int. Cl.$^4$ ............................ C25B 1/14; C25B 3/04
[52] U.S. Cl. ................................. 204/58.5; 204/59 R
[58] Field of Search ............................ 204/58.5, 59 R

[56] References Cited

U.S. PATENT DOCUMENTS

| | | | |
|---|---|---|---|
| 2,855,353 | 10/1958 | Huff et al. | 204/59 |
| 3,117,032 | 1/1964 | Panzer | 136/4 |
| 3,413,154 | 11/1968 | Rao | 136/100 |
| 3,445,290 | 5/1969 | Elliot et al. | 136/83 |
| 3,508,966 | 4/1970 | Eisenberg | 136/6 |
| 3,542,601 | 11/1970 | Gabano | 136/155 |
| 3,594,120 | 7/1971 | Bott et al. | 23/91 |
| 3,904,432 | 9/1975 | Dey | 136/6 LN |
| 3,981,748 | 9/1976 | Margalit | 429/164 |
| 3,998,658 | 12/1976 | Dey | 429/194 |
| 4,113,929 | 9/1978 | Margalit | 429/194 |
| 4,184,017 | 1/1980 | Kelsey et al. | 429/197 |
| 4,187,350 | 2/1980 | McIntyre et al. | 429/45 |
| 4,223,079 | 9/1980 | Margalit et al. | 429/194 |
| 4,229,509 | 10/1980 | Margalit et al. | 429/194 |
| 4,423,124 | 12/1983 | Dey | 429/194 |
| 4,488,943 | 12/1984 | Skotheim | 204/58.5 |

OTHER PUBLICATIONS

Derwent Publications 02962x/02 (1970), 00753x/01 (1973), 46607B/25 (1974), 58862x/31 (1974), 119164/07 (1975), 117184/07 (1975), 84–00456/11 (1982).
Chem. Abstracts 75:57859q.
Derwent Publications, 46607B/25, L03, R47, Matsushita Elec Ind KK, J7 9012–609.
Derwent Publications, E17 L03 R47 (E13), Matsushita Elec Ind KK, J5 1070–418.
Derwent Publications, 11916Y/07, L03 R47, Hitachi Maxell, J5 2000 330.
Derwent Publications, 11918Y/07, L03 R47, Hitachi Maxell, J5 2000 332.
Derwent Publications, 8 –064546/11, E32 L03 U11 (E12), UK SEC for Defence, GB 2125-795-A.

*Primary Examiner*—John F. Niebling
*Assistant Examiner*—David G. Ryser
*Attorney, Agent, or Firm*—N. Jerome Rudy

[57] ABSTRACT

Included is an invention, which in one aspect, is a process for preparing a product of an alkaline earth metal compound having at least one BVB-heteromoeity and by-product of an alkali metal substance comprising operating an electrochemical cell, said cell having (1) a sacrificial alkaline earth metal anode,
(2) a liquid electrolyte, which contains a solvent that is generally inert and a solute that has at least a residual alkali metal moiety and an incorporatable BVB-heteromoiety therein, and
(3) an alkali metal substance segregative cathode, under conditions whereby said product and by-product are prepared. Provided, among other products, are alkaline earth metal organoborates. For example, magnesium triethylpyrrolylborate can be prepared by employing a magnesium anode, a solution of lithium triethylpyrrolylborate in tetrahydrofuran and a cupric oxide and carbon containing cathode. Intercalating cathodes can provide electrical current output.

20 Claims, No Drawings

ALKALINE EARTH METAL COMPOUNDS AND ALKALI METAL SUBSTANCES VIA ELECTROCHEMICAL PROCESS

FIELD

This invention concerns metallic compositions of matter, with a procedure, that is, a method and/or process, for their preparation. These compositions are generally useful chemical reagents.

BACKGROUND

Production of certain alkaline earth metal compounds, including those which can be employed as a componen in dry batteries, for example, magnesium tetrafluoroborate and magnesium hexafluorophosphate, espeeially in dry batteries of the "button" variety such as disclosed, for example, by Dey in U.S. Pat. No. 3,998,658 (1976), can be problematical at best. For example, typical ion exchange procedures, which any person skilled in the art might attempt to employ to prepare such compounds or compounds of even a more exotic nature such as alkaline earth metal boron organic compounds, by cation exchange of a corresponding alkali metal compound for the alkaline earth are generally ill-suited for, or even inoperative in, such production. Huff et al., U.S. Pat. No. 2,855,353 (1958), discloses a particular process for preparing certain alkaline earth metal borohydrides such as those of magnesium or calcium, which employs a mercury or mercuric cathode and a non-aqueous solvent such as ammonia, pyridine, certain amines or higher ethers such as polyethylene glycol dimethyl ethers.

Therefore, one of ordinary skill in the art might attempt to employ another procedure should he desire such alkaline earth metal compounds, especially in any kind of practical quantity or quality. Heretofore, a serious lack and a certain need in the art included a process which can efficiently prepare, or even provide, such alkaline earth metal compounds.

SUMMARY

The invention, in one aspect, is a process for preparing a product of an alkaline earth metal compound having at least one BVB-heteromoiety and by-product of an alkali metal substance comprising operating an electrochemical cell, said cell having (1) a sacrificial alkaline earth metal anode, (2) a liquid electrolyte, which contains a solvent that is generally inert and a solute that has at least a residual alkali metal moiety and an incorporatable BVB-heteromoiety therein, and (3) an alkali metal substance segregative cathode, under conditions whereby said product and by-product are prepared. Separating at least one of said product or by-product from a remaining portion of said cell optionally follows. Another aspect is a novel product such as an alkaline earth metal compound having at least one boron containing organic heteromoiety, which can be prepared by the process of the invention.

The invention promotes progress in the useful arts because the process of the invention is very efficient and can be operated in a very controllable manner; and it can be most substantially selective in preparing said product and by-product and can prepare alkaline earth metal compounds which are not readily synthesizable exclusively by conventional chemical, including ion-exchange, procedures. A hallmark of the invention is that, in addition to preparing a multitude of well known useful alkaline earth metal compounds, it provides many novel compounds such as those selected from the alkaline earth metal compounds having at least one boron containing organic heteromoiety. An additional feature of the invention is that it prepares useful alkali metal substances. Thus, the process of the invention is of the utmost utility.

More particularly, the alkaline earth metal compounds are useful chemical intermediates, reagents such as appropriate reducing agent, cleaving agents such as for ester or ether hydrolysis, agents for providing a hydrogen or lower alkane atmosphere, additives for pyrotechnic displays, chelating agents, dry battery electrolyte solutes and so forth. The alkali metal substances are generally well known chemical intermediates, reagents for useful chemical syntheses, or are useful, for example, as an electrode or as a solute in an electrolyte and so forth.

DETAILED DESCRIPTION

The mentioned product of the process of the invention is the alkaline earth compound having at least one BVB-heteromoiety. Said product contains a residue of an alkaline earth metal, typically which has at least a formal, if not ionic, charge therein of positive two.

The alkaline earth metals are Beryllium (Be), Magnesium (Mg), Calcium (Ca), Strontium (Sr), Barium (Ba) and Radium (Ra). Preferred of these include Mg, Ca, Sr and Ba, specifically, Mg.

The alkaline earth cbmpound has at least one BVB-heteromoiety. Preferably, the overall sample of said product contains BVB-heteromoieties and alkaline earth metal residues in a BVB-heteromoiety to alkaline earth metal equivalent ratio of from about 1:2 to about 2.5:1, more preferably about 1:1 to about 2:1 and most preferably about 2:1.

The BVB-heteromoiety is a multicomponent moiety such as those which contain at least one residue of an element such as a low molecular weight Boron group element such as Boron (B), even aluminum (Al), preferably B, or a high pnicogen, that is, a high molecular weight element of group VB (American System) of the Periodic Table. The high pnicogens are herein Phosphorus (P), Arsenic (As), Antimony (Sb) and Bismuth (Bi), with P, As and Sb being preferred.

Each BVB-heteromoiety typically has a formal, if not ionic, charge of minus one. Representative examples of BVB-heteromoieties include those such as the following generally inorganic moieties: borohydride, borodeuteride, cyanoborohydride (cyanotrihydridoborate), cyanoborodeuteride, tetrafluoroborate, tetrachloroborate, tetrabromoborate, tetraiodoborate, chlorotrifluoroborate, tetrahydridoaluminate, tetrachloroaluminate, hexafluorophosphate, hexafluoroarsenate, hexafluoroantimonate, and so forth and the like. Preferably, such generally inorganic moiety is such as the tetrafluoroborate, hexafluorophosphate and hexafluoroarsenate moieties, and most preferably, the tetrafluoroborate moiety. The BVB-heteromoiety can also be an organoborate moiety. The organoborate moiety is especially preferred.

The organoborate moiety is the boron containing organic heteromoiety such as is present in the novel product of the invention. The organoborate moieties are preferably represented by the simple formula:

$$BQ_mR_n^-, \qquad (I)$$

wherein
- the "B" represents a boron residue, in general, formally B(III), which is tetravalent within the organoborate moiety itself;
- the "Q" represents, separately at each occurrence, a moiety such as hydrido (H), which may be termed "hydride" within the organoborate moiety, or halido (including F; Cl; Br; I), which may be termed "halo", for example, "fluoro", within the organoborate moiety, preferably the hydrido or fluorido, and more so the hydrido moiety;
- the "R" represents, separately at each occurrence, a monovalent, divalent, trivalent or tetravalent, as appropriate, organido moiety ("organo"), preferably the monovalent or divalent, and more so the monovalent, with the organido moiety being an organic moiety having the appropriate formal negative charge;
- the "m" represents, separately at each occurrence, an integer from zero to three, preferably zero or one, more so zero; and
- the "n" represents, separately at each occurrence, an integer from one to four, as appropriate, preferably from two to four, more so four.

Thus, because the boron residue of the organoborate moiety of the simple formula (I) is tetravalent within the organoborate moiety itself, the sum of the "m" and "n" values in the organoborate moieties of the simple formula (I) can be at most, and most preferably is equal to, four, and this sum of "m" plus "n" is at least one, as is appropriate to the separate valence of each organido (R) moiety bonded to the boron residue (B). For example, with the "m" value equal to zero, the "n" value can be equal to two, either with one of the monovalent and one of the trivlent "R" moieties, or with two of the divalent "R" moieties.

Each organido (R) moiety of the organoborate moiety is advantageously a $C_{1-20}$ (from one to about twenty carbon(s)) organido moiety. Each organido moiety is preferably a hydrocarbylido, such as ranging from an alkylido, for example, methylido, ethylido, a butylido and so forth, to an arenido, for example, phenylido, benzylido, a toluedylido, a napthylido and so forth, or a substituted hydrocarbon moiety such as those substituted with one or more of an ether (R'—O—R'), thioether (R'—S—R') or azine (R'—NR'—R'; R'=N—R') moiety, but is more preferably substituted with a so-called OSN-moiety such as an oxy (R"O—), thioxy (R"S—) or disubstituted amino (R"—NR"—) moiety.

The O, S and N of the latter are each preferably bonded to the boron residue. Examples of the latter include pyrrolyl and N-methylanilino and N-n-butylanilino.

The "R'" moieties are appropriately organic and include cyclic moieties and heterocyclic moieties with the O, S or N but are preferably $C_{1-10}$ hydrocarbyl, especially alkyl.

The "R''" moieties are appropriately organic and include cyclic moieties and heterocyclic moieties with the O, S or N. A morpholinyl moiety is an example of an OSN-moiety also having an ether linkage therein. A thiomorpholinyl moiety is an example of an OSN-moiety also having a thioether linkage therein. Other such substitutions are readily available to any person skilled in the art. However, each "R''" moiety is preferably $C_{1-10}$ hydrocarbyl, but more preferably $C_{2-4}$ alkyl including those which are integrally heterocyclic with the O, S, or N especially with the N of the disubstituted amino moieties, for example, as in the pyrrolyl moiety.

The novel product of the invention thus may include alkaline earth metal organoborates. The alkaline earth metal organoborates are preferably represented by the simple general formula:

$$MB'_xY_{(2-x)}, \qquad (II)$$

wherein
- the "M" is the residue of the alkaline earth metal;
- the "B'" is, separately at each occurrence, an organoborate moiety such as is represented by the simple formula (I);
- the "Y" is an appropriate inorganic countermoiety other than the "B'", typically having a formal, if not ionic, charge of minus one, such as, for example, fluoride, chloride, bromide, iodide, perchlorate, and so forth and the like, most preferably chloride, and
- the "x" is the integer one or two, preferably two.

Representative examples of the alkaline earth metal organoborates of the simple general formula (II) include those such as
- beryllium triethylborohydride;
- magnesium triethylborohydride;
- magnesium triethylborodeuteride;
- magnesium tri-sec-butylborohydride;
- magnesium triisobutylborohydride;
- magnesium trisiamylborohydride;
- magnesium thexyllimonylborohydride;
- magnesium trimethoxyborohydride;
- magnesium triisopropoxyborohydride;
- calcium tetraethylborate;
- magnesium tetraethylborate;
- magnesium triethyl-n-hexylborate;
- magnesium triethyl-n-propoxyborate;
- magnesium triethylthioxyethylborate;
- magnesium triethyl-N-methylanilinoborate;
- magnesium triethylpyrrolylborate;
- magnesium trisiamylpyrrolylborate;
- strontium triethylpyrrolylborate;
- barium triethylpyrrolylborate;
- radium triethylpyrrolylborate;
- magnesium thexyllimonylboroethide;
- magnesium thexyllimonylboroethoxide;
- magnesium thexyllimonylboropyrrolylide;
- magnesium tetraphenylborate, and so forth and the like.

More generally, the alkaline earth metal compounds having at least one BVB-heteromoiety are preferably represented by the following simple general formula:

$$MB''_xY_{(2-x)}, \qquad (III)$$

wherein
- the "M", "Y" and "x" are each as set forth in the simple general formula (II), and
- the "B''" is, separately at each occurrence, the BVB-heteromoiety, which, of course, includes those such as the organoborate moieties such as, for instance, the "B'" moiety of the alkaline earth metal organoborates of the simple general formula (II), and the generally inorganic BVB-heteromoieties such as, for example, the tetrafluoroborate moiety.

Representative examples of alkaline earth metal compounds having at least one BVB-heteromoiety, in addition to the alkaline earth metal organoborates, include the generally inorganic alkaline earth metal compounds having at least one BVB-heteromoiety such as
  beryllium borohydride;
  beryllium tetrafluoroborate;
  magnesium borohydride;
  magnesium borodeuteride;
  magnesium cyanoborohydride;
  magnesium cyanoborodeuteride;
  magnesium tetrafluoroborate;
  magnesium chlorotrifluoroborate;
  magnesium tetrahydridoaluminate;
  magnesium tetrachloroaluminate;
  magnesium hexafluorophosphate;
  magnesium hexafluoroarsenate;
  magnesium hexafluoroantimonate;
  magnesium trifluoromethanesulfonates;
  calcium borohydride;
  calcium tetrafluoroborate;
  calcium tetrachloroborate;
  calcium hexafluorophosphate;
  calcium trifluoromethanesulfonates;
  strontium borohydride;
  strontium tetrafluoroborate;
  strontium tetrachloroborate;
  strontium hexafluorophosphate;
  strontium trifluoromethanesulfonates;
  barium borohydride;
  barium tetrafluoroborate;
  barium tetrabromoborate;
  barium hexafluorophosphate;
  barium trifluoromethanesulfonates;
  radium borohydride;
  radium tetrafluoroborate;
  radium tetraiodoborate;
  radium hexafluorophosphate;
  radium trifluoromethanesulfonates;
and so forth and the like.

Said by-product of the process of the invention is the alkali metal substance. This by-product is, or contains and is a derivative of, an alkali metal. The derivative may have a formal charge on the alkali metal of zero such as, for instance, in a metal alloy with the alkali metal or may have a formal, if not ionic, positive charge of typically positive one, such as, for instance, in a binary alkali metal salt, oxide or sulfide. Certain derivatives may have an overall formal, if not ionic, charge from zero to, say, about one such as, for instance, in an intercalate containing alkali metal residue.

The alkali metals include Lithium (Li), Sodium (Na) which is also known as Natrium, Potassium (K), Rubidium (Rb) and Cesium (Cs). Francium (Fr) is also an alkali metal, but the occurrence of Fr is so rare that it makes francium substances and residues insignificantly existent however enabling in the present invention. Preferred of these include Li, Na, K and Rb, more so Li, Na and K, specifically so, Li.

Representative examples of the alkali metal substances include those such as
  the elemental alkali metal;
  an alloy of a plurality of the alkali metals;
  an appropriate alloy of the alkali metal with a metal such as aluminum (Al), Mg, tin (Sn) and/or lead (Pb);
  titanium disulfide and Li intercalate;
  lithium oxide;
  lithium hydroxide and lithium methoxide;
  lithium sulfide;
  sodium oxide;
  sodium sulfide;
  potassium sulfide;
  and so forth and the like.

The sacrificial anode (sacrificial alkaline earth metal anode) of the electrochemical cell employed in the process of the invention contains alkaline earth metal. Preferably, the sacrificial anode at least consists essentially of the pure alkaline earth metal, for example, magnesium.

The liquid electrolyte also contains, or is reacted to contain, the incorporatable BVB-heteromoiety, which is incorporatable into said product and thus corresponds to the BVB-heteromoiety of the alkaline earth metal compound which is prepared by the process of the invention. Thus, the incorporatable BVB-heteromoiety can include those such as the mononegative tetrafluoroborate anion; the mononegative borohydride anion and the like, as appropriate; a mononegative organoborate anion; the mononegative hexafluorophosphate anion; the mononegative hexafluoroarsenate anion, and so forth. Other ions may be present, for example, chloride or Al(III).

The liquid electrolyte contains a residual alkali metal moiety. The alkali metal of the residual alkali metal moiety generally corresponds to the alkali metal substance by-product which is prepared by the process of the invention.

The liquid electrolyte is a liquid during the electrochemical cell operation. The liquid itself is generally considered a solvent such as a cyclic or straight chain ether or thioether, an alkylene carbonate, an alkyl carbonyl nitrile, a cyclic ester, a dialkyl formamide or a dialkyl sulfoxide, for example, diethyl ether, diethyl sulfide, 1,3-dithiolane, (dl)-4-hydroxypentanoic lactone, propylene carbonate, acetonitrile, dimethyl formamide, dimethyl sulfoxide, and so forth and the like. Of the ethers, more specifically preferred for preparing the alkaline earth metal borohydrides, especially of Mg and Ca, are the cyclic ethers. Even liquids including such alcohols, for example, as methanol, may be employed with the less reactive solutes such as, for example, sodium borohydride. Liquid ammonia, pyridine, or amines, especially trialkyl amines, for example, triethylamine, may be employed for preparing the halogen or cyanide moiety containing borates, all the aluminates or all the organoborates of the alkaline earth metals, as well. Trialkyl amines may be employed for preparing the Mg and Ca borohydrides and borodeuterides herein. A mixture of such solvents can be employed, as appropriate. Preferred are the aprotic solvents, including the trialkyl amines. A preferred class of the aprotic solvents includes $C_{4-8}$ cyclic alkyl ethers such as 1,4-dioxane, tetrahydrofuran, 2-methyltetrahydrofuran and so forth. Most preferred of the aprotic solvents include those such as tetrahydrofuran; 2-methyltetrahydrofuran and acetonitrile, especially tetrahydrofuran (THF).

Examples of the aprotic electrolyte which can be initially employed include systems such as 0.5 M lithium hexafluoroarsenate in tetrahydrofuran; 0.5 M lithium hexafluorophosphate in 2-methyl-tetrahydrofuran; 0.5 M lithium tetrafluoroborate in tetrahydrofuran; 0.5 M lithium tetrafluoroborate, 0.5 M lithium chloride and 0.5 M aluminum trichloride in tetrahydrofuran; 0.5 M potassium hexafluorophosphate in acetonitrile; 0.5 M lithium tetra-n-butylborate in tetrahydrofuran; 0.25 M lithium triethylmonopyrrolylborate in tetrahydrofuran; 1.0 M lithium triethylmonopyrrolylborate in tetrahydrofuran; and so forth. In general, the more suitable concentrations of solutes such as the residual alkali metal compounds, including those with the incorporatable BVB-heteromoiety, initially range from about 0.1 M to the upper limit of solubility of the solute. For the most part, a generally satisfactory upper limit to the initial concentration of the solute is about 3 M. Commonly, the initial concentration of the solute ranges about the value of 0.5 M such as is found within the preferred initial range of solute concentration, which is from about 0.25 M to about 1.5 M.

The residual alkali metal moiety and incorporatable BVB-heteromoiety solute and solvent electrolyte mixture can be thus provided by means well known to any person skilled in the art. Preferably, the electrolyte mixture is provided by simply dissolving an alkali metal compound having the BVB-heteromoiety therein.

The alkali metal compounds having the BVB-heteromoiety therein are well known and readily available; see, for example, Rao, U.S. Pat. No. 3,413,154 (1968); Gabano, U.S. Pat. No. 3,542,601 (1970) and Dey, U.S. Pat. No. 4,423,124 (1983) each of these three U.S. patents incorporated herein by reference), or they can be readily prepared by a known procedure or by a procedure such as disclosed herein. For example, from the readily commercially available lithium triethylborohydride (e.g., Aldrich Chemical Co.), can be readily prepared lithium triethylpyrrolylborate by slowly adding pyrrole to a 1.0 M solution of lithium triethylborohydride in tetrahydrofuran under a dry nitrogen blanket. Others can be similarly prepared.

For instance, in general, alkali metal organoborates can be prepared, as appropriate, by the following illustrative procedures (I and II), with illustrative procedure (1) being

$$BQ_3 + n'LiR \rightarrow BQ_{(3-n')}R_{n'} + LiQ_{n'} \quad (Ia)$$

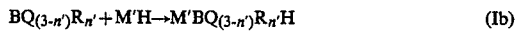

$$BQ_{(3-n')}R_{n'} + M'H \rightarrow M'BQ_{(3-n')}R_{n'}H \quad (Ib)$$

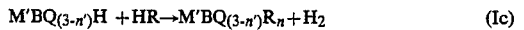

$$M'BQ_{(3-n')}H + HR \rightarrow M'BQ_{(3-n')}R_n + H_2 \quad (Ic)$$

and illustrative procedure (II) being

$$BQ_3 + 4M'R \rightarrow M'BR_4 + 3M'Q \quad (II)$$

wherein each of the illustrative procedures (I and II)
the "LiR" is an exemplary alkylating agent of the general formula "M'R", which may be replaced, as appropriate, by an agent such as a Grignard reagent and the like;
the "n '" is equal to the value of "n" minus one;
the "Q", "R", "M'" and "n" are as in the foregoing formulae (I, II and III), and
the "B" and "H" representing appropriate residues of boron or hydrogen, respectively.

An inert diluent may be employed in such procedures.

In general, the alkali metal substance segregative cathode is a cathodic system which can segregate the alkali metal substance from remaining electrolyte and the alkaline earth metal compound having at least one BVB-heteromoiety (said product) which is prepared. More particularly, the alkali metal substance segregative cathode is preferably one which can electroplate, intercalate or react with the residual alkali metal moiety of the electrolyte in carrying out the process of the invention. Mercury (Hg) may be absent therefrom.

The alkali metal substance segregative cathode which can electroplate, in general, is capable of electroplating the alkali metal substance as a metallic element about the cathode. Examples of the electroplating cathode itself include those such as containing carbon or metals such as, for example, Al, nickel (Ni), copper (Cu), iron (Fe), even Mg and combinations or alloys thereof, for example, steel. The use of the aluminum or magnesium electroplating cathodes typically results in electroplating of the alkali metal substance as the appropriate alloy, for example, LiAl or LiMg. Inert substances may also be present. In conjunction with the electroplating cathode, a separator between the anode and cathode must be present. Suitable separators are well known in the art, and thus the separator can be one such as those of filter paper as disclosed by Dey in U.S. Pat. No. 3,998,658 (1976) and Dey et al. in U.S. Pat. No. 3,904,432 (1975) or of a glass mat, cellophane, microporous polypropylene, microporous polytetrafluoroethylene or microporous polysulfide as disclosed by Margalit in U.S. Pat. No. 3,981,748 (1976) (each of these three U.S. Pat. Nos. incorporated herein by reference).

The alkali metal substance segregative cathode which can react with, in general, is capable of reacting with an alkali metal substance such as the alkali metals. The reacting cathode typically forms a substance, such as, for example, the alkali metal oxide or sulfide, which is preferably at most sparingly soluble and more preferably insoluble in the aprotic electrolyte. Examples of the reacting cathode include those such as cupric oxide, manganese dioxide, vanadium pentoxide, molybdenum trioxide, and so forth and the like, for example, cupric sulfide, and so forth. Preferred are cupric oxide and cupric sulfide.

The alkali metal substance segregative cathode which can intercalate, in general, is capable of intercalating the alkali metal substance, typically as a metallic element, within the cathode. Examples of the intercalating cathode include those such as titanium disulfide and intercalating cathodes which contain certain metal oxides, for example, a chromium trioxide and graphite intercalation compound cathode as disclosed by Dey, supra. Preferred is titanium disulfide. Lithium metal is most preferably a component of the intercalate.

Of the foregoing three types of preferred alkali metal substance segregative cathodes, the intercalating and reacting cathodes are the most interesting because in contrast to employment of the electroplating cathodes, employment of the intercalating and reacting cathodes generally requires no power input, such as may be most often found in operating in the electrochemical cell of the process of the invention. Thus, electrochemical cells of the process of the invention having the intercalating and reacting cathodes not only prepare said product and by-product but also can be generally operated in the additionally useful primary (generally non-rechargeable battery) mode. Thus, an additionally useful product of an electric current can be prepared in this manner.

In operating the electrochemical cell, conditions which can prepare said product and by-product and so forth can vary widely. In addition to the foregoing conditions, including parameters, the following conditions and parameters of the process of the invention, including temperature, pressure, voltage, current density, time and separating technique, are preferably employed, as appropriate.

Because the electrolyte is a liquid during the electrochemical cell operation, temperatures of the process of the invention reside from about the freezing point to about the boiling point of the specific electrolyte system which is employed. As a lower limit, a temperature of about −40° C. is often preferably suitable; more preferably, the lower limit is about 0° C. As an upper limit, temperatures within the range of about 60° C. to about 250° C. are typically preferably suitable, as appropriate to the electrolytic system which is employed; more preferably, the upper limit is about 50° C. Most preferably, the temperature is generally ambient such as, for example, from 20° C. to 30° C.

In general, the pressure of the process of the invention can be from supra- to subatmospheric. More preferably, the pressure is ambient such as about normal atmospheric pressure, for example, from about 95 kPa to about 105 kPa.

In the electrolytic mode, the input of practically any applied (positive) voltage from where reaction of the process of the invention up to the applied voltage which may cause electrolyte decomposition can be employed. More preferably, the applied voltage generally resides in the range from 1 volt (V) to 4 V.

In general, the current density is important only insofar as it affects the voltage. As a rule, for example, in the electrolytic mode, as the current density is increased, there is an increase in the applied voltage.

The electrochemical process of the invention is operated for that time which, in conjunction with the other process conditions and parameters, is sufficient for preparing said product and by-product. In general, the time of the operation of the electrochemical process can range, more or less, from 10 minutes to five score (100) hours. More preferably, the electrochemical process is carried out for the measure of time generally ranging from one hour to two score (40) hours.

Nearly any size and generally any appropriate variety of cell itself can be employed in the process of the invention. Suitable cells are readily apparent or well known to any person skilled in the art. See, e.g., McIntyre et al., U.S. Pat. No. 4,187,350 (1980) (incorporated herein by reference). A preferred cell size is from about 250 milliliters (mL) to about 4 liters (L). Most preferably, the aprotic electrolyte in the cell is mixed during the cell operation such as by stirring, for example, with a magnetic stirring bar which is coated with polytetrafluoroethylene.

An optional step of the process of the invention is the separating of at least one of said product(s) and by-product(s) from the remaining portion of the cell. Well known techniques are generally employed. Preferred are filtration, evaporation of liquid and/or chromatography, as appropriate and desired.

The following example further illustrates the invention. Percentages and so forth are by weight unless otherwise specified.

EXAMPLE—GALVANIC SYNTHESIS OF MG—ORGANOBORATES

An electrolytic cell is constructed with a commercially pure Mg anode, a cathode of 50 percent CuO, 30 percent graphite powder, 20 percent polytetrafluoroethylene binder pressed into a cavity in a steel rod, and a 1.0 M $LiB(C_2H_5)_3$ pyrrole/tetrahydrofuran (THF) electrolyte. The cell exhibits an initial O.C.P. (Open Circuit Potential) of 1.16 V which climbs to 1.30 V following a brief current pulse of 5.0 mA (milliamperes). The cell is discharged across a 1.00 kΩ (kiloohm)/load for 24 hours and averages about 0.2–0.3 V. Upon the completion of this period, the O.C.P. is about 0.5 V, indicating a significant cathode utilization. Atomic absorption spectroscopic analysis of the electrolyte indicates a Mg to Li molar equivalent ratio of 5:1, with B below detection limits. The Mg displaces the Li in the electrolyte solution.

If the THF of the solution is evaporated and the residue of the electrolyte is analyzed by infrared spectroscopy, most substantial amounts of magnesium triethylpyrrolylborate are detected. If further recovery and purification of this product is carried out by solid/liquid chromatography, a substantial amount of highly pure magnesium triethylpyrrolylborate is recovered.

Many changes and modifications can readily be made and adapted in specifically altered embodiments in accordance with the present invention without substantially or materially departing from its apparent and intended spirit and scope, all in pursuance and accordance with same as it is set forth and defined in the hereto-appended claims.

What is claimed is:

1. A process for preparing a product of an alkaline earth metal compound having at least one BVB-heteromoiety selected from a group consisting of borohydride, borodeuteride, cyanoborohydride (cyano-trihydridoborate), cyanoborodeuteride, tetraflouro-borate, tetrachloroborate, tetrabromoborate, tetra-iodoborate, chlorotrifluoroborate, tetrahydrido-aluminate, tetrachloroaluminate, hexafluorophosphate, hexafluoroarsenate and hexaluoroantimonate, beryllium triethylborohydride, magnesium triethylborohydride, magnesium triethylborodeuteride, magnesium tri-sec-butylborohydride, magnesium triisobutylborohydride, magnesium trisiamylborohydride, magnesium thexyllimonylborohydride, magnesium trimethoxyborohydride, magnesiium triisopropoxyborohydride, calcium tetraethylborate, magnesium tetraethylborate, magnesium triethyl-nhexylborate, magnesium riethyl-n-propoxyborate, magnesium triethylthioxyethylborate, magnesium triethyl-N-methylanilinoborate, magnesium triethylpyrrolylborate, magnesium trisiamylpyrrolylorate, strontium triethylpyrrolylborate, barium triethylpyrrolyborate, radium triethylpyrrolyborate, magnesium thexyllimonylboroethide, magnesium thexyllimonylboroethoxide, mangesium thexyllimonylboropyrrolylide, magnesium tetraphenylborate, beryllium borohydride, beryllium tetrafluoroborate, magnesium borohydride, magnesium borodeuteride, magnesium cyanoborohydride, magnesium cyanoborodeuteride, magnesium tetrafluoroborate, magnesium chlorotrifluoroborate, magnesium tetrahydridoaluminate, magnesium tetrachloroaluminate, magnesium hexafluorophosphate, magnesium hexafluoroarsenate, magnesium hexafluoroantimonate, magnesium trifluoromethanesulfonates, calcium borohydride, calcium tetrafluoroborate, calcium tetrachloroborate, calcium hexafluorophosphate, calcium trifluoromethanensulfonates, strontium borohydride, strontium tetrafluoroborate, strontium tetrafluoroborate, stontium tetrachloroborate, strontium hexafluorophosphate, stontium trifluoromethanesulfonates, barium borohydride, barium tetrafluoroborate, barium tetrabromoborate, barium hexafluorophosphate, barium trifluoromethanesulfonates, radium borohydride, radium tetrafluorborate, radium tetraiodoborate, radium hexafluorophosphate, and radium trifluoromethanesulfonates in an electrochemical cell, said cell having (1) a sacrificial alkaline earth metal anode, (2) a liquid electrolyte, which contains a solvent that is generally inert and at least a residual alkali metal moiety and a BVB-heteromiety, and (3) a cathode, by applying an electromotive force between the anode and the cathode, provided that if the alkaline earth metal compound having at least one BVB-heteromoiety is a product selected from the group consisting of magnesium borohydride, magnesium borodeuteride, calcium brohydride and calcium borodeuteride, the solvent is selected from the group consisting of a thioether, a cyclic alkyl ether, an alkylene carbonate, an alkyl carbonyl nitrile, a cyclic ester, a dialkyl fromamide, a dialkyl sulfoxide, a trialkyl amine, a dialkylaryl amine, a diarylalkyl amine and a triarylamine, and said cathode contains no mercury and thereafter separating the alkaline earth metal compound from the cell and recovering the alkaline earth metal compound from the electrolyte.

2. The process of claim 1 wherein the BVB-heteromoiety is inorganic.

3. The process of claim 2 wherein the alkaline earth metal contains magnesium.

4. The process of claim 3 wherein the alkali metal is selected from the group consisting of lithium, sodium and potassium.

5. The process of claim 4 wherein said product containing the magnesium compound having at least one inorganic BVB-heteromoiety is separated from the remaining portion of said cell.

6. The process of claim 5 wherein the solvent is aprotic.

7. The process of claim 6 wherein the solvent is tetrahydrofuran.

8. The process of claim 7 wherein the alkali metal is lithium.

9. The process of claim 8 wherein said product contains a magnesium compound selected from the group consisting of magnesium tetrafluoroborate, magnesium hexafluorophosphate, magnesium hexafluoroarsenate and magnesium trifluoromethanesulfonate.

10. The process of claim 8 wherein said product is magnesium borohydride.

11. The process of claim 1 wherein the BVB-heteromoiety contains an organoborate moiety.

12. The process of claim 11 wherein said product is an alkaline earth metal organoborate represented by the general formula:

$$M(BQ_mR_n)_xY(2-x),$$

wherein

M is the residue of the alkaline earth metal;

B is a boron residue which is tetravalent within the organoborate moiety itself;

Q is separately at each occurrence a moiety selected from the group consisting of hydrido and halido;

R is separately at each occurrence a mono- to tetravalent $C_{1-20}$ organido moiety;

Y is an inorganic countermoiety;

m is an integer from zero to three;

n is an integer from one to four, and x is the integer one or two.

13. The process of claim 12 wherein the M is selected from the group consisting of Be, Mg, Ca, Sr and Ba, and the R is mono- or divalent.

14. The process of claim 13 wherein the Q is hydrido;

the m is zero or one, and the n is an integer from two to four.

15. The process of claim 14 wherein the M is zero, and the x is two.

16. The process of claim 15 wherein the M is Mg.

17. The process of claim 16 wherein the R is moiety selected from the group consisting of a $C_{1-10}$ hydrocarbylido moiety and a $C_{1-10}$ OSN-moiety.

18. The process of claim 17 wherein the organoborate moiety is triethylpyrrolylborate.

19. The process of claim 2 wherein the inorganic BVB-heteromoiety is selected from the group consisting of borohydride, borodeuteride, cyanoborohydride (cyano-trihydridoborate), cyanoborodeuteride, tetraflouro-borate, tetrachloroborate, tetrabromoborate, tetra-iodoborate, chlorotrifluoroborate, tetrahydridoaliminate, tetrachloroaluminate, hexfluorophosphate, hexafluoroarsenate and hexafluoroantimonate.

20. The process of claim 1 wherein an electromotive force is applied between the anode and an alkali metal substance segregative cathode.

* * * * *

UNITED STATES PATENT AND TRADEMARK OFFICE
CERTIFICATE OF CORRECTION

PATENT NO. : 4,808,282
DATED : February 28, 1989
INVENTOR(S) : Thomas D. Gregory It is certified that error appears in the above-identified patent and that said Letters Patent is hereby corrected as shown below:

Col. 1, line 15, "componen" should read -- component --;

line 17, "espeeially" should read -- especially --.

Col. 2, line 32, "cbmpound" should read -- compound --.

Col. 3, line 36, "trivlent" should read -- trivalent --.

Col. 10, line 26, "tetraflouro-borate" should read -- tetrafluoroborate --;

line 27, "tetra-iodoborate" should read -- tetraiodoborate --;

line 28, "tetrahydrido-aluminate" should read -- tetrahydroaluminate --;

line 30, "hexaluoroantimonate" should read -- hexafluoroantimonate --;

line 36, "magnesiium" should read -- magnesium --;

line 38, triethyl-nhexylborate" should read -- triethyl-n-hexylborate --;

UNITED STATES PATENT AND TRADEMARK OFFICE
CERTIFICATE OF CORRECTION

PATENT NO. : 4,808,282

DATED : February 28, 1989

INVENTOR(S) : Thomas D. Gregory

Page 2 of 3

It is certified that error appears in the above-identified patent and that said Letters Patent is hereby corrected as shown below:

Col. 10, lines 38-39, "riethyl-n-propoxyborate" should read -- triethyl-n-propoxyborate --;

lines 41-42, "trisiamylpyrrolylorate" should read -- trisiamylpyrrolylborate --;

lines 42-43, "triethylpyrrolyborate" should read -- triethylpyrrolylborate --;

line 43, "triethylpyrrolyborate" should read -- triethylpyrrolylborate --;

line 45, "mangesium" should read -- magnesium --;

line 57, "trifluoromethanensulfonates" should read -- trifluoromethanesulfonates --;

line 59, "stontium" should read -- strontium --;

line 60, "stontium" should read -- strontium --;

line 64, "tetrafluorborate" should read -- tetrafluoroborate --.

Col. 11, line 3, "BVB-heteromiety" should read --BVB-heteromoiety--.

line 10, "brohydride" should read -- borohydride --;

line 13, "fromamide" should read -- formamide --.

UNITED STATES PATENT AND TRADEMARK OFFICE
CERTIFICATE OF CORRECTION

PATENT NO. : 4,808,282
DATED : February 28, 1989
INVENTOR(S) : Thomas D. Gregory It is certified that error appears in the above-identified patent and that said Letters Patent is hereby corrected as shown below:

Col. 12, lines 39-40, "tetraflouro-borate" should read
-- tetrafluoroborate --;

line 41, "tetra-iodoborate" should read -- tetraiodoborate --;

line 42, "hexfluorophosphate" should read
-- hexafluorophosphate --.

In the Abstract, line 3, "BVB-heteromoeity" should read
-- BVB-heteromoiety --.

Signed and Sealed this

Twenty-seventh Day of March, 1990

Attest:

JEFFREY M. SAMUELS

Attesting Officer

Acting Commissioner of Patents and Trademarks